(12) United States Patent
Tomoda et al.

(10) Patent No.: US 6,434,422 B1
(45) Date of Patent: Aug. 13, 2002

(54) METHOD AND APPARATUS FOR JUDGING RECOVERY OF PHYSICAL CONDITION IN PUERPERIUM

(75) Inventors: Shoji Tomoda, Sakai; Syuji Ueda, Osaka; Kentaro Kimura, Tokyo, all of (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/653,951

(22) Filed: Sep. 1, 2000

(30) Foreign Application Priority Data

Sep. 3, 1999 (JP) .............................................. 11-250650

(51) Int. Cl.$^7$ ................................................. A61B 5/00
(52) U.S. Cl. ....................................... 600/547; 600/551
(58) Field of Search ................................ 600/547, 551, 600/587, 591

(56) References Cited

FOREIGN PATENT DOCUMENTS

WO          WO92/19153          11/1992

OTHER PUBLICATIONS

European Search Report dated Dec. 4, 2000.
"Equipment using an impedance technique for automatic recording of fluid–volume changes during haemodialysis", B. Tedner, Medical & Biological Engineering & Computing, vol. 21, May 1, 1983, pp. 285–290.
"Total body water in pregnancy: assessment by using biolectric impedance$^{1-3}$", Henry C. Lukaski et al., The American Journal of Clinical Nutrition, vol. 59, No. 3, Mar. 1994, pp. 578–584.

*Primary Examiner*—Max Hindenburg
(74) *Attorney, Agent, or Firm*—McDermott, Will & Emery (57) ABSTRACT

Disclosed is a method and apparatus for judging a recovery of physical condition of a puerperal woman, wherein a bioelectric characteristic of the puerperal woman is measured and a value thereof is stored, and the recovery of her physical condition is judged based on the variation thereof. Further, the bioelectric characteristic of the woman in non-pregnancy period or at an early stage of her pregnancy period and the bioelectric characteristic of the puerperal woman are measured, and the recovery of her physical condition after delivery is judged based on the comparison between these bioelectric characteristics.

28 Claims, 11 Drawing Sheets

| CURRENT DATE | 2000 | YEAR | 01 | MONTH | 04 | DAY |
|---|---|---|---|---|---|---|
| DELIVERY DATE | 1999 | | 12 | | 30 | |

AFTER DELIVERY 05 DAY

| BODY WEIGHT IN NON-PREGNANCY PERIOD | 50kg | RECOVERY | 96% |
|---|---|---|---|
| CURRENT BODY WEIGHT | 52kg | SATISFACTORY RECOVERY | |
| ELECTRIC IMPEDANCE IN NON-PREGNANCY PERIOD | 500 Ω | RECOVERY | 90% |
| CURRENT ELECTRIC IMPEDANCE | 455 Ω | SATISFACTORY RECOVERY | |
| INTERSTITIAL FLUID INDEX IN NON-PREGNANCY PERIOD | 20.0 | RECOVERY | 90% |
| CURRENT INTERSTITIAL FLUID INDEX | 22.0 | SATISFACTORY RECOVERY | |

▽  SET  △

FIG. 6b

METHOD AND APPARATUS FOR JUDGING RECOVERY OF PHYSICAL CONDITION IN PUERPERIUM

BACKGROUND OF THE INVENTION

1. Field of the Invention

The present invention relates to a method and an apparatus for judging recovery of physical condition of a puerperal woman, for example, for determining whether or not to allow her to be discharged from the hospital.

2. Description of the Prior Art

Conventionally, judgment of the recovery of physical condition of a puerperal woman is based on such that if she can stand up, then she would be allowed to start walking. Further, although a doctor has made a decision on discharge of the woman in puerperium from the hospital by taking all the results of blood test and urinalysis in addition to good uterine contraction into account, it generally has been the practice that woman is discharged from the hospital about one week after her delivery.

However, the woman in her puerperium is subjected to a considerable burden which could not be determined by her external appearance since the woman's body after delivery is significantly changed from one environment to grow a placenta inside a uterus to the other environment to nurse a newborn outside the uterus. For example, since the puerperal woman can not hold inside a blood vessel an amount of blood having been increased due to pregnancy, a blood pressure increases to cause a blood plasma leaking from the blood vessel into an intercellular substance, which eventually produces an internal body change caused by retaining a large amount of water content in the intercellular substance, i.e. a large edema, even after her delivery.

SUMMARY OF THE INVENTION

The present invention is to measure a bioelectric characteristic of a puerperal woman as well as to store a value of the measured bioelectric characteristic, and to judge a recovery of her physical condition after delivery based on the variation of the values.

Further, the present invention is to measure a bioelectric characteristic of a woman in non-pregnancy period or at an early stage of her pregnancy period as well as that in her puerperium after delivery, so that these bioelectric characteristics may be compared each other to make a right judgment regarding a recovery of her physical condition after delivery.

Still further, the recovery of the physical condition of a puerperal woman is to be judged by the comparison of the bioelectric characteristic value of the woman in non-pregnancy period or at an early stage of her pregnancy period with a variation in the bioelectric characteristic value in her puerperium after delivery.

Still further, preferably the bioelectric characteristic is a bioelectric impedance.

Still further, preferably the bioelectric characteristic is an interstitial fluid index.

Still further, the present invention provides an apparatus comprising a measuring unit which measures a bioelectric characteristic of a puerperal woman, a storing unit which stores a value of the bioelectric characteristic, and an indicating unit which indicates data having stored in the storing unit.

Furthermore, the present invention provides an apparatus comprising a measuring unit which measures a bioelectric characteristic of a woman in non-pregnancy period or at an early stage of her pregnancy period, and a bioelectric characteristic of the puerperal woman, a storing unit which stores measured values of these bioelectric characteristics, a comparing unit which compares the value of the bioelectric characteristic in non-pregnancy period or at the early stage of her pregnancy period with the value of the bioelectric characteristic in her puerperium after delivery, each of said values of the bioelectric characteristics having been stored in said storing unit, and an indicating unit which indicates the data in said comparing unit.

Still further, preferably said measuring unit measures a bioelectric impedance of a woman in her puerperium and said indicating unit indicates an impedance value.

Still further, preferably said measuring unit measures an interstitial fluid index of a woman in her puerperium period and said indicating unit indicates the interstitial fluid index.

Still further, preferably said storing unit stores the bioelectric characteristic in her non-pregnancy period or at an early stage of her pregnancy period and a daily bioelectric characteristic in her puerperium period after delivery.

Furthermore, the present invention provides a method for judging a recovery of physical condition of a puerperal woman comprising the steps of: measuring a bioelectric characteristic of the woman in non-pregnancy period or at an early stage of her pregnancy period; measuring the bioelectric characteristic of the puerperal woman; storing said bioelectric characteristics; and graphically indicating said bioelectric characteristics to facilitate a judgment of the recovery of physical condition of the puerperal woman.

Still further, said bioelectric characteristics to be stored for her non-pregnancy period and for up to around 12th week in her pregnancy period is a mean value of the bioelectric characteristics averaged over around one week.

Furthermore, the present invention provides an apparatus for judging a recovery of physical condition of a puerperal woman comprising: a measuring unit which measures a bioelectric characteristic of a woman in non-pregnancy period or at an early stage of her pregnancy period and the bioelectric characteristic of the puerperal woman; a storing unit which stores measured values of said bioelectric characteristics; and an indicating unit which graphically indicates said bioelectric characteristics stored by said storing unit.

There will now be described in detail preferred embodiments of the present invention with reference to the drawing.

DESCRIPTION OF THE PREFERRED EMBODIMENTS

Figure 1:
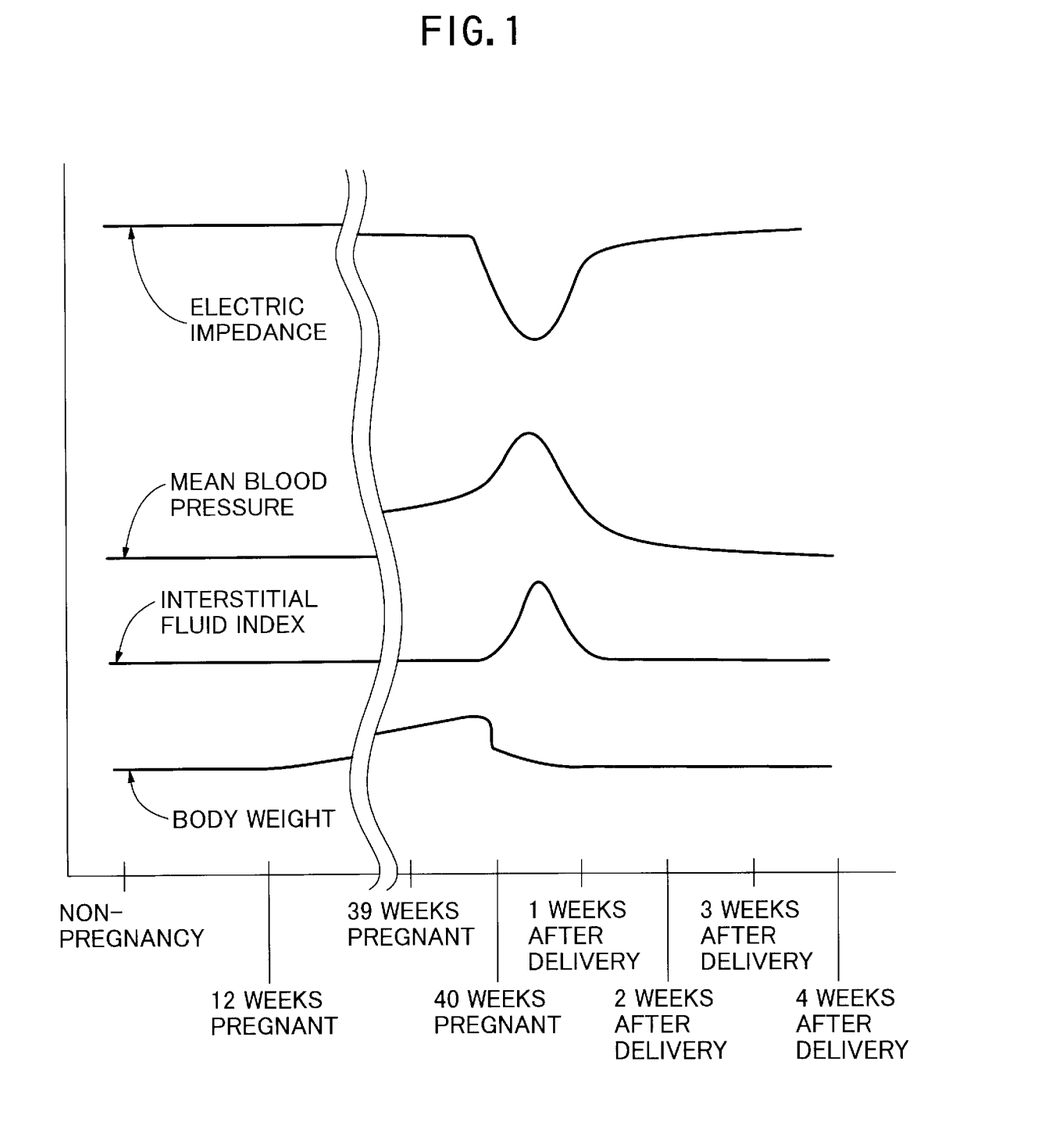
FIG. 1 is a graphical representation showing a condition of a woman before pregnancy through to after delivery.

Referring now to FIG. 1, it graphically represents a variation of a woman's physical condition during the period before pregnancy through to delivery (herein, 39 weeks and 5 days) and thereafter by measuring, for example, 4 variables including a body weight, a mean blood pressure, an electric impedance representative of a bioelectric characteristic, and an interstitial fluid index which is determined by multiplying the inverse of the electric impedance by 1000. According to the measurement, little change is shown as to before pregnancy up to an early stage of pregnancy, i.e. up to around 12 weeks, but after 12 weeks a gradual rise of the body weight corresponding to a fetus growing is observed, which does not return to the former level as before pregnancy even with a drop at the time of child birth, and returns to almost the same weight as before pregnancy more than 2 weeks after the delivery. The mean blood pressure is shown to develop a tendency to decrease toward a middle stage of pregnancy until the latter period as approaching to a delivery when the uterine contraction causes the blood pressure to rise. Since a vessel is constricted after the delivery, the mean blood pressure is shown to keep on rising for first few days after the delivery, subsequently fall down rapidly in another few days, and finally, when 3 weeks or more has past after the delivery, return to the mean blood pressure of the non-pregnancy period. These variations in the body weight and in the mean blood pressure right after the delivery represent that an amount of blood which has been increased for nurturing a fetus and a nutrition which has been internally accumulated in the blood and the body do not decrease immediately after the delivery, but to decrease gradually over about one week.

Further, the electric impedance is shown to decline slightly over the weeks of pregnancy, rapidly drop immediately after the delivery and for following one week approximately, and subsequently recover in next one to two weeks. Since the interstitial fluid index in FIG. 1 interlocks with the inverse of the electric impedance, it changes in an opposite direction upwardly or downwardly with respect to the electric impedance. This decrease in the electric impedance immediately after the delivery is considered to be caused by the increased extracellular fluid which results from the increased amount of blood due to the pregnancy temporarily leaking into the intercellular substance because of the rise in the blood pressure. Especially in a woman suffering from preeclampsia, since the extracellular fluid has been significantly increased, i.e. having a large edema produced, the electric impedance is held to be low, which takes long time to return to an original level.

Thus, it is possible to judge how the physical condition in the puerperium after delivery has been recovered by measuring the electric impedance or the bioelectric characteristic representative of the interstitial fluid index after the delivery and by tracing the variation thereof or comparing the measured value with the bioelectric characteristic measured in the non-pregnancy period or at the early stage of pregnancy.

Figure 2:
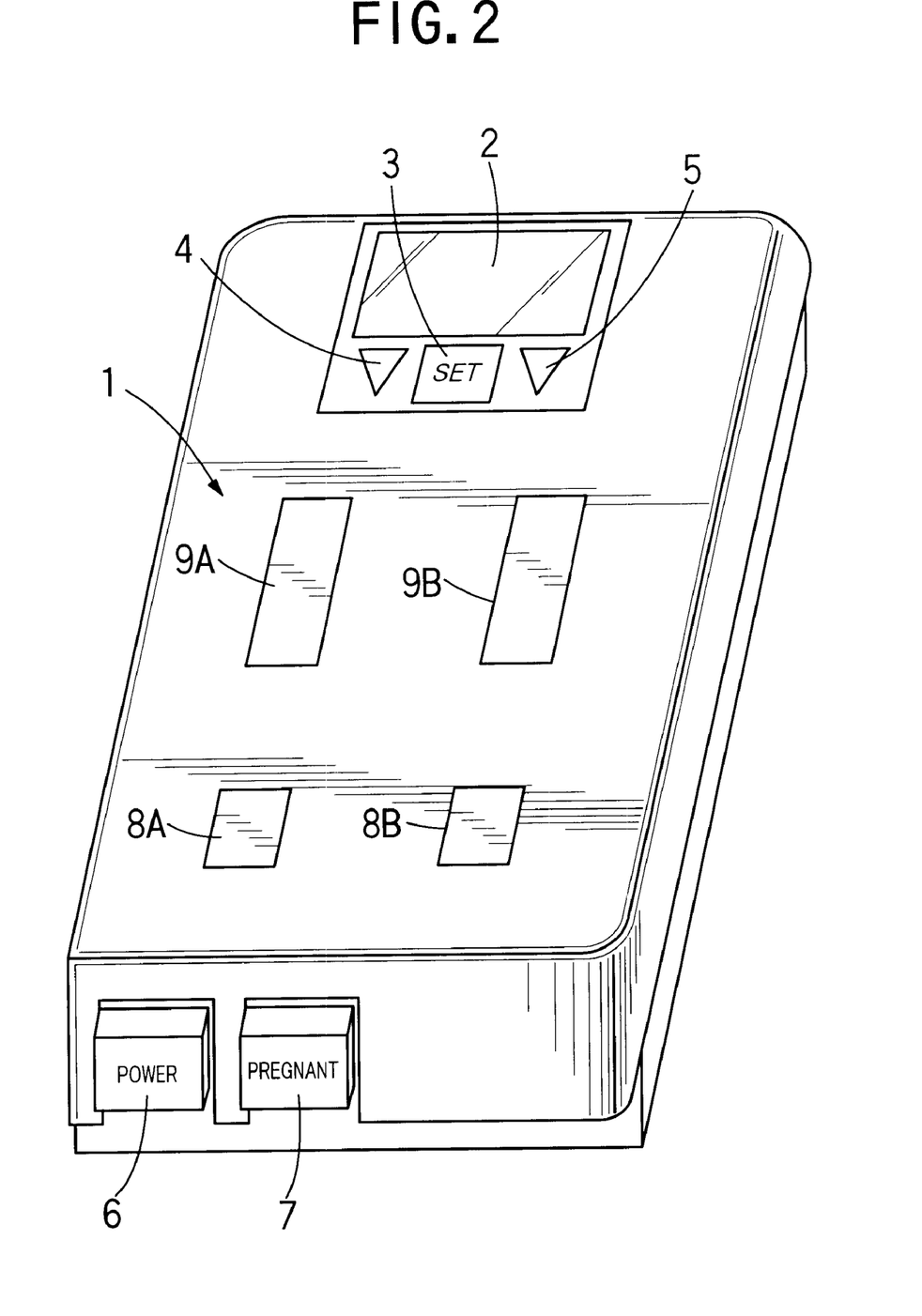
FIG. 2 is a schematic perspective view of an apparatus for measuring a recovery of physical condition.

FIG. 2 is a schematic perspective view of an apparatus for measuring a recovery of physical condition according to the present invention. Reference numeral 1 designates a main body of the apparatus for measuring the recovery of physical condition, which includes a known weight scale therein and further comprises thereon an indicator section 2, a data set push button 3 for inputting various data, a down button 4 for decreasing a data value, and an up button 5 for increasing a data value. Reference numeral 6 designates a power switch. Reference numeral 7 designates a change-over switch for switching the apparatus to be used as a regular weight scale or as a weight scale for a pregnant woman. Reference numerals 8A and 8B designate electrodes with which a left and a right heels are to be brought into contact respectively, and reference numerals 9A and 9B designate electrodes for a left and a right toes respectively.

Figure 3:
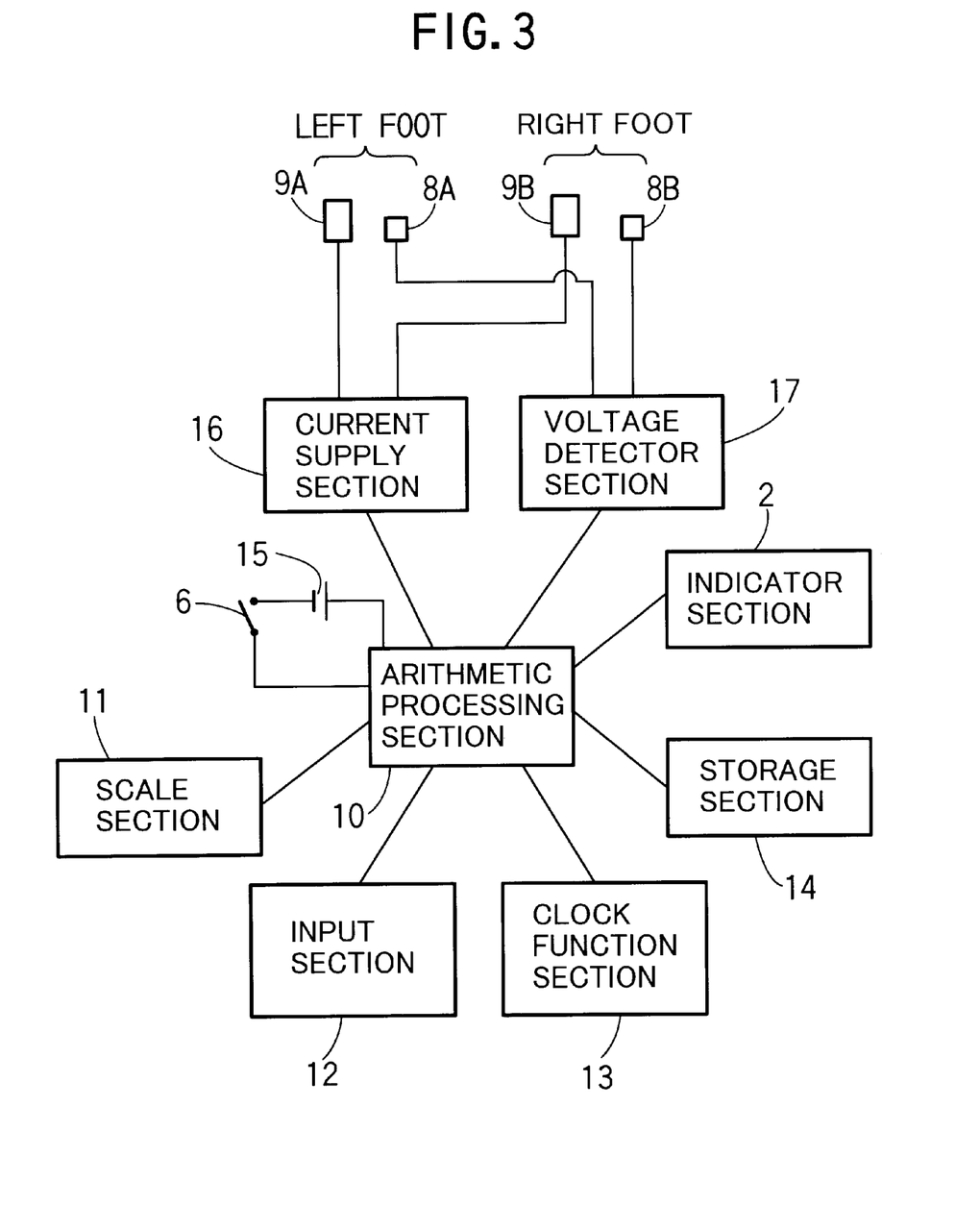
FIG. 3 is a schematic block diagram of an electric circuit of the apparatus for measuring the recovery of physical condition.

FIG. 3 is a schematic block diagram of an electric circuit of the apparatus 1 for measuring the recovery of physical condition shown in FIG. 2. Reference numeral 10 designates an arithmetic processing section made up of micro computer, which is connected to a well-known scale section 11 for measuring a body weight, an indicator section 2, an input section 12 including the set button 3, the down button 4, the up button 5 and the change-over switch 7, a known clock function section 13, and a nonvolatile storage section 14 for storing data such as results of the calculation. Reference numeral 15 designates a battery which is connected to the arithmetic processing section 10 via the power switch 6 and also supplies electricity to other sections that need electricity.

Reference numeral 16 designates a current supply section which is connected to the arithmetic processing section 10 and supplies constant current to the electrodes 9A and 9B for the left and the right toes in response to the signals from the arithmetic processing section 10, and reference numeral 17 designates a voltage detector section which is connected to the arithmetic processing section 10 and measures the voltage applied between the electrode 8A for the left heel and the electrode 8B for the right heel in response to the signals from the arithmetic processing section 10.

Figure 4:
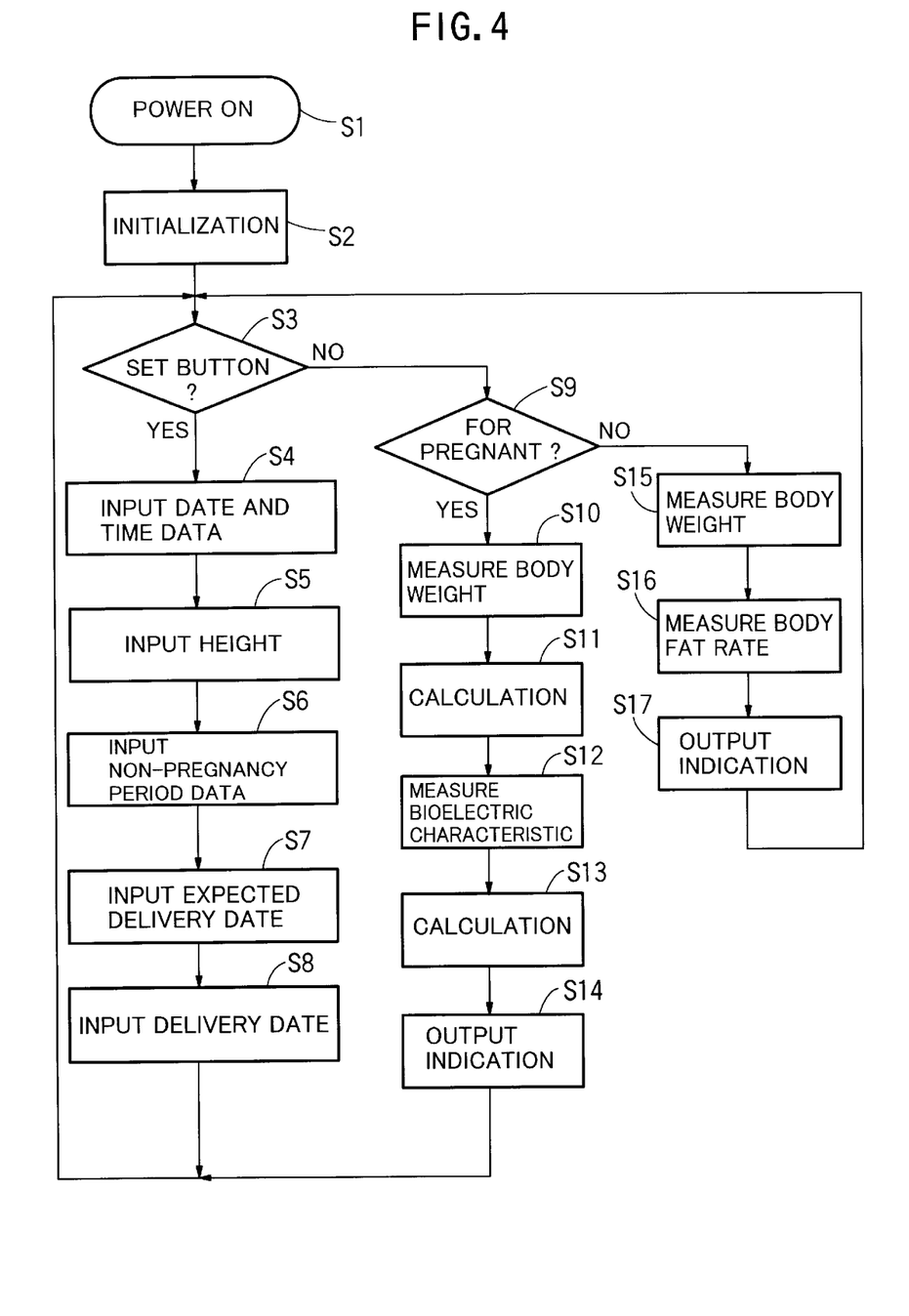
FIG. 4 is a flow chart of the apparatus for measuring the recovery of physical condition.

FIG. 4 is a flow chart for measuring the recovery of physical condition according to the present invention.

FIGS. 5a to 5e and 6a and 6b show an indicator section 2 with several input data and the results of measurement being indicated thereon respectively.

Figure 5A:
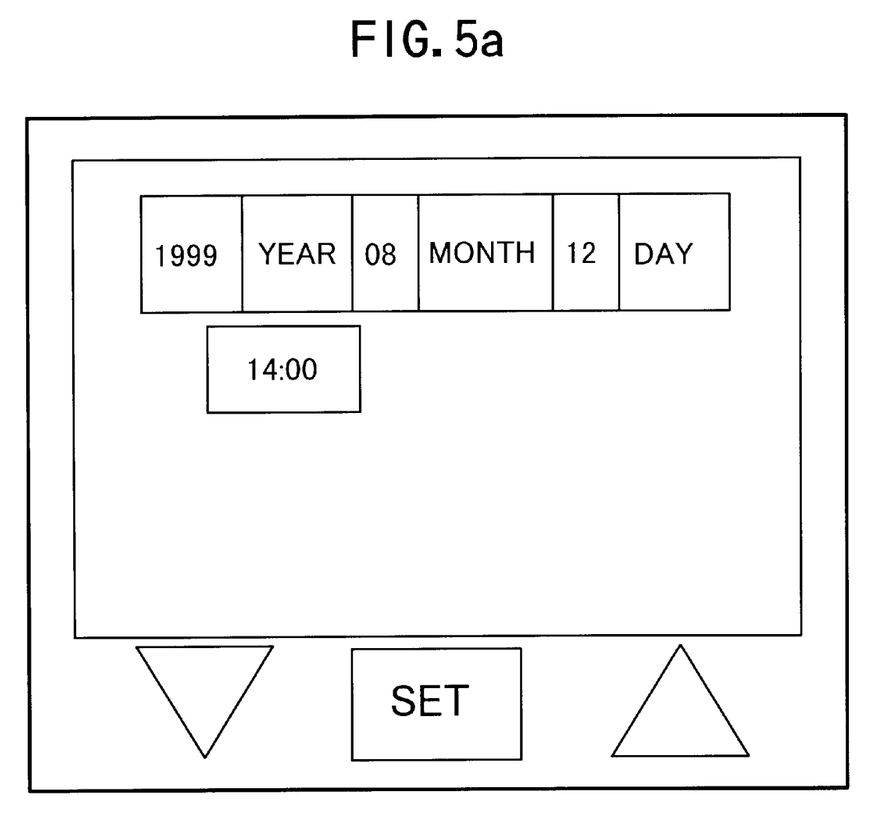
FIGS. 5a to 5e show an indicator section of the apparatus for measuring the recovery of physical condition with several input data being indicated thereon respectively.

Now the operation of the present apparatus will be described with reference to FIGS. 2 to 4 and FIGS. 5a to 5e and 6a and 6b. At first the power switch 6 of the apparatus 1 for measuring the recovery of physical condition is pressed to supply the electricity to the arithmetic processing section 10 and other sections from the battery 15 (step S1). This initializes the microcomputer incorporated in the arithmetic processing section 10 (step S2). In step 3, whether the set button 3 has been pressed or not is determined and, if pressed, then the process moves to step 4 where the current date is set as shown in FIG. 5a. Because this setting operation is broadly known and practiced with many devices, the detailed description will be omitted herein, but in brief, initially the up button 5 and/or the down button 4 are to be pushed to match a year indication to the current year and then the set button 3 is to be pushed to set month. Thus, when the indications of the month, day, hour, and minute are matched to the current ones and the set button 3 is pushed in the similar manner, the input of the current date and time is completed and the process moves to step S5. The clock function section 13 is configured to work independently, even if the power switch 6 being turned off, to adjust the date and the time based on those having been set at step S4 and to indicate always the current date and time on the indicator section 2 whenever the power switch 6 is turned on next time.

Figure 5B:
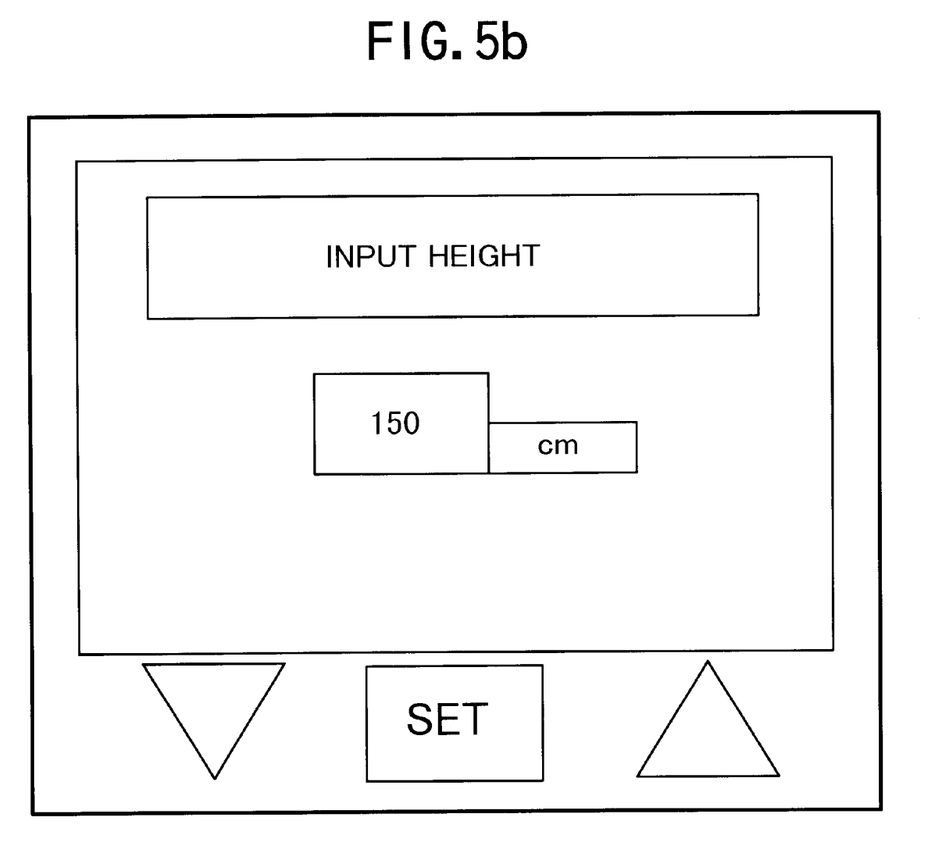
Figure 5C:
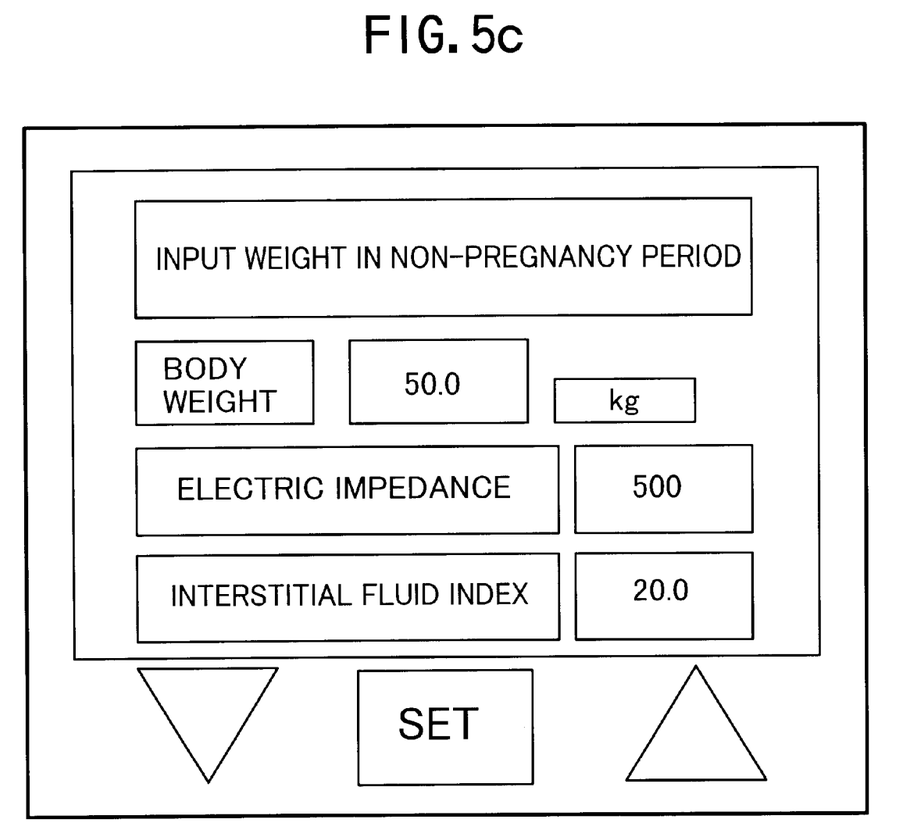

At step S5, the height of the pregnant woman is input using the up key 5 or the down key 4 to adjust the value as desired starting from the initial indication of 150 cm on the indicator section 2 as shown in FIG. 5b. Then the set key 3 is pushed to store the value in the storage section 14. The height stored at this step is used for further arithmetic processing. Now the process moves to step S6. Step S6 is provided for inputting the weight, the electrical impedance and the interstitial fluid index before pregnancy, i.e. in the non-pregnancy period or in an early stage of pregnancy, and since the initial values are indicated, as shown in FIG. 5c, as 50 kg for the body weight, 500 Ω for the electric impedance, and 20 for the intercellular substance water content index respectively on the indicator section 2, at first the up key 5 or the down key 4 is used to change the body weight value as desired and the set button 3 is pushed to store the set body weight value in the storage section 14, then the up key 5 or the down key 4 is used to change the electric impedance value as desired and the set button 3 is pushed to store the set impedance value in the storage section 14, and finally the up key 5 or the down key 4 is used to change the interstitial fluid index value as desired and the set button 3 is pushed to store the set value of interstitial fluid index in the storage section 14. The data for non-pregnancy period stored at this step is used for further arithmetic processing. Now the process moves to step S7.

Figure 5D:
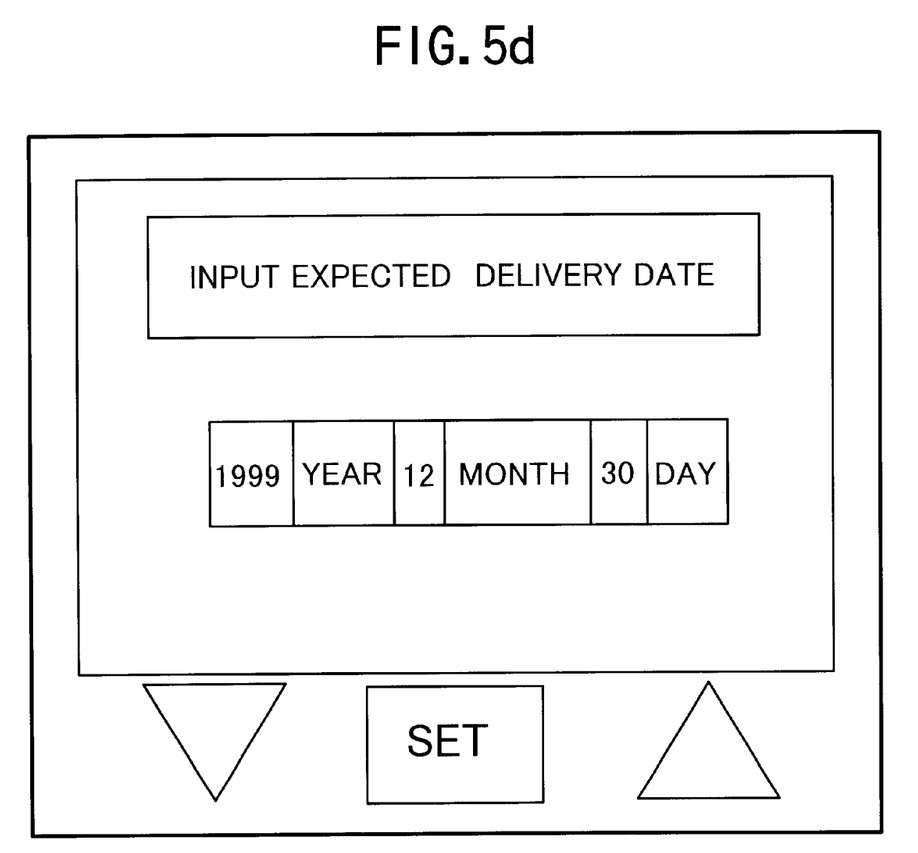
Figure 5E:
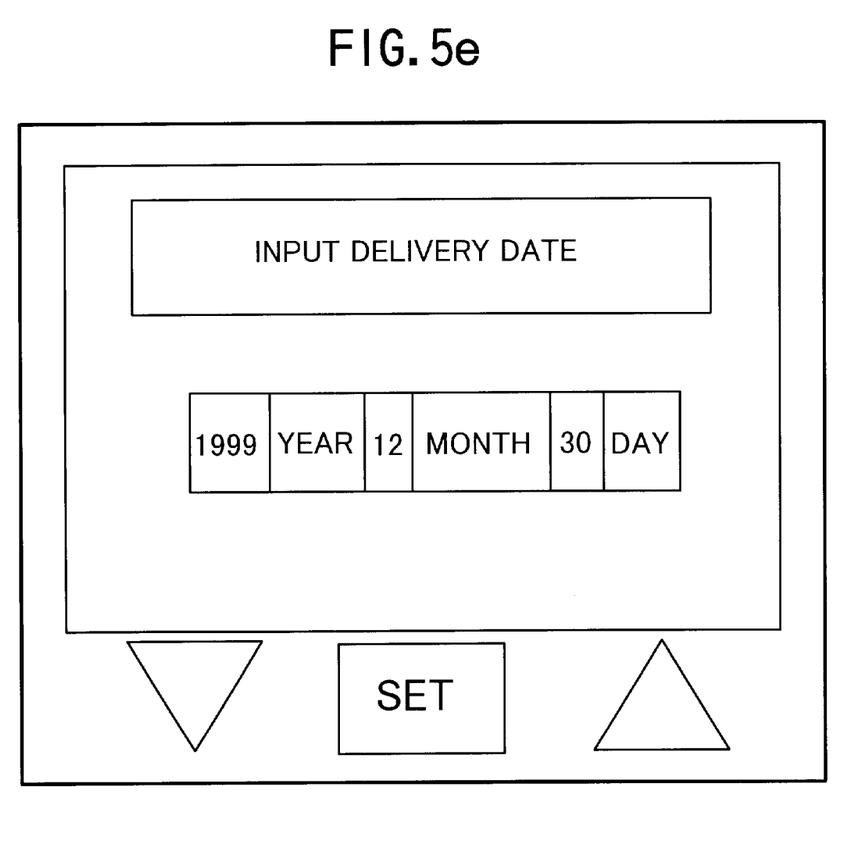

At step S7, as shown in FIG. 5d, an expected date of delivery according to a diagnosis by an obstetrician is input as year, month and day in the same manner as set in step S4, and the set button 3 is pushed to store the data for the expected date of delivery in the storage section 14, and then the process moves to step S8. At this step S8, the date of the delivery is set as shown in FIG. 5e in the same manner as described in step S7 and the set button 3 is pushed to store the date of the delivery in the storage section 14. In the case where exclusively the date of the delivery is to be input later, since, as to the data to be set at steps S4 through to S7, the set data have been stored in the storage section 14 and thereby the indicator section 2 indicates the stored data, the set button 3 may be pushed to make the process move to step S8.

Once the data has been set as described above, unless the set button 3 is pressed again, the process determines at step S3 to be NO and moves to step S9. At step S9, when the change-over switch 7 has been pressed, the apparatus is considered to work as the weight scale for a pregnant woman and the process moves to step S10 where the body weight is measured with the left foot placed on the electrodes 8A and 9A and the right foot on the electrodes 8B and 9B, each electrode being located on the upper surface of the apparatus 1 for measuring the recovery of physical condition. The body weight measured at this step are stored along with the data for the date of measurement in the storage section 14, which are used for the arithmetic processing at step S11. At step S11, the body weight in the non-pregnancy period input at step S6 is compared with the current body weight to calculate how the latter is approaching close to the former one.

Figure 6A:
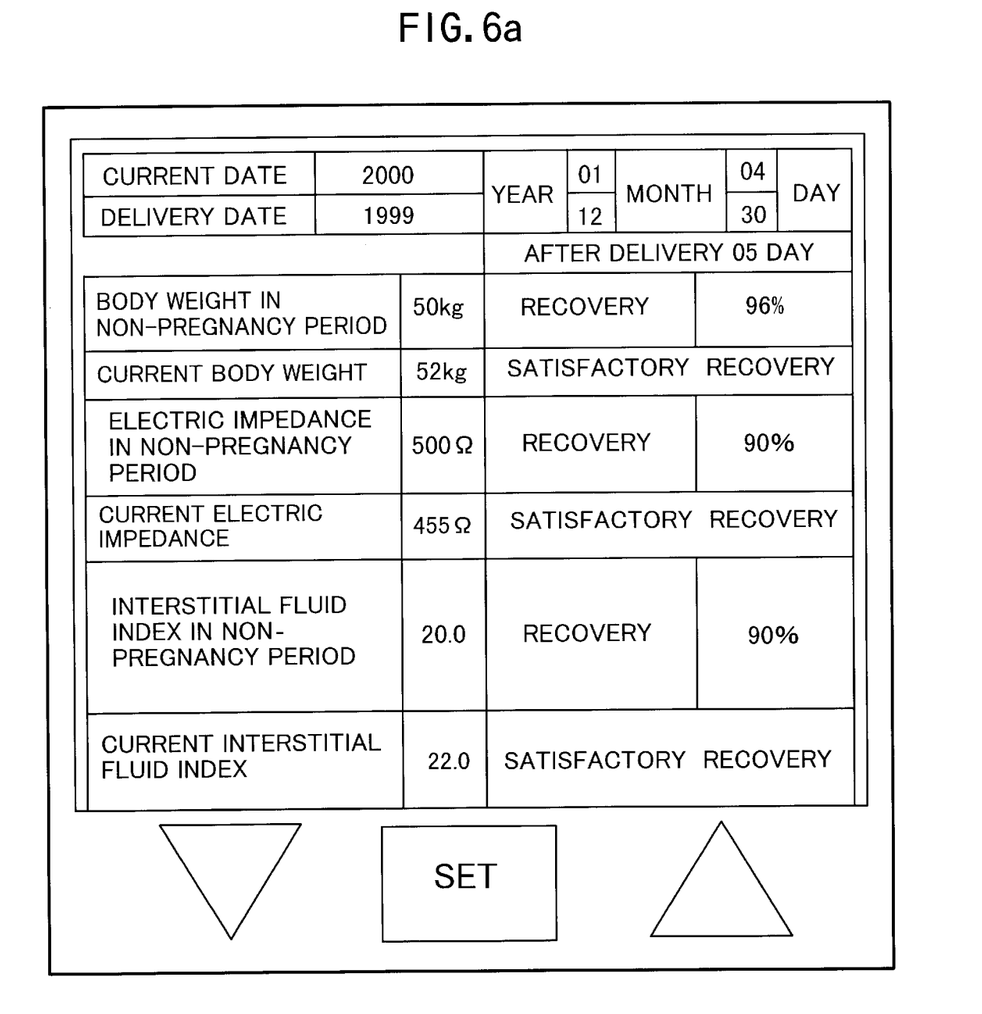
FIGS. 6a and 6b show an indicator section of the apparatus for measuring the recovery of physical condition with the results of the measurement being indicated thereon respectively.

At step S12, a weak current is applied from the current supply section 16 through the electrodes 9A and 9B to the left foot and the right foot of the pregnant woman and the voltage is measured between the electrodes 8A and 8B. Since the principle for this measurement is the same with that of a known body fat measuring apparatus, the detailed description thereof will be omitted. Now in step S13, the bioelectric impedance is calculated from the measured current and voltage and also the interstitial fluid index is calculated. In this step, the electric impedance and the interstitial fluid index in the non-pregnancy period or at the early stage of pregnancy are further compared with those of currently measured to calculate and determine how the electric impedance and the interstitial fluid index are recovering toward those measured in the non-pregnancy period or at early stage of pregnancy. At step S14, the results of this calculation are indicated on the indicator section 2 as shown in FIG. 6a and the process returns back to step S3.

Figure 6B:
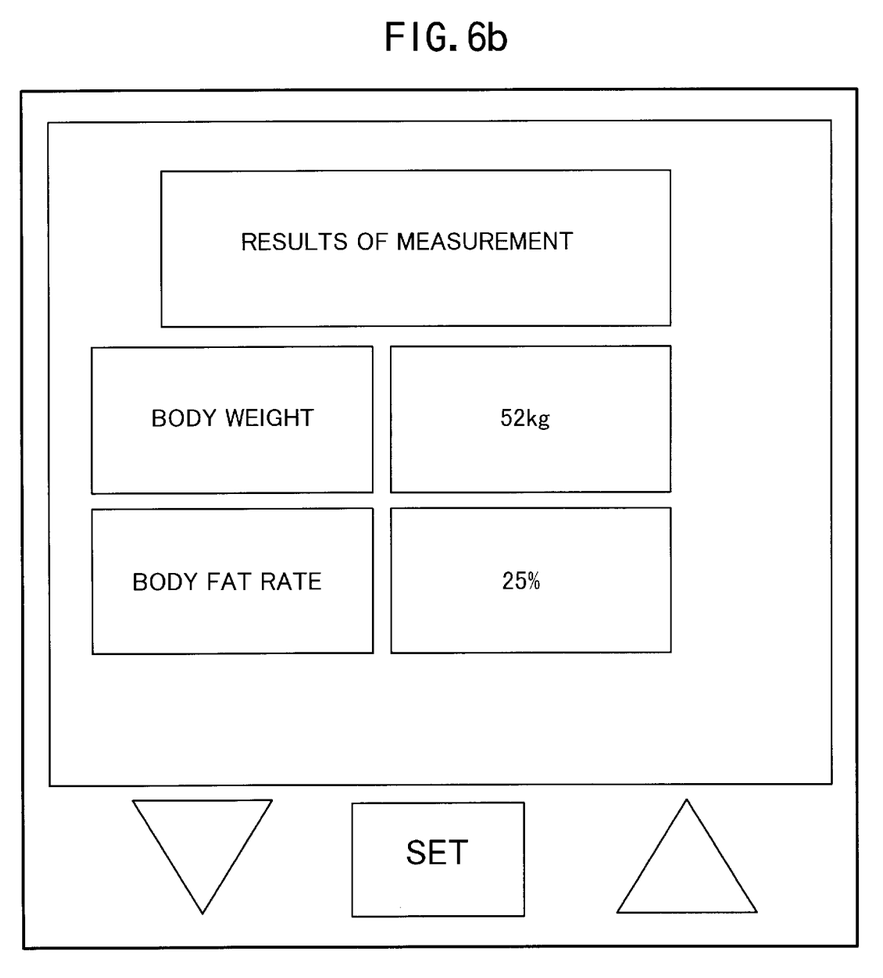

Further, when the process determines to be NO at step S9, the body weight is measured at step S15, the electric impedance is measured at step S16 in the same manner as of step S12, and the body fat rate is calculated using the principle for a well-known body fat measuring apparatus. The result is indicated on the indicator section 2 at step S17 as shown in FIG. 6b, and the process returns back to step S3.

Although, in the present embodiment, the variations of both of the electric impedance and the interstitial fluid index are indicated, only the interstitial fluid index may be indicated since the recovery of physical condition may be represented only by the interstitial fluid index.

Further, although, in the present embodiment, the variations of the body weight and the electric impedance, i.e. the interstitial fluid index are used to measure the recovery of physical condition, it is recommendable that the recovery of the mean blood pressure would be taken into account in order to make the measurement more precise.

Still further, although, in the present embodiment, the bioelectric characteristic in the non-pregnancy period or at the early stage of pregnancy is compared with the bioelectric characteristic in the puerperium after delivery, only the absolute value of the bioelectric characteristic in the puerperium after delivery may be used for the judgment if the bioelectric characteristic in the non-pregnancy period or at early stage of pregnancy could not have been measured.

Yet further, although, in the present embodiment, the data before the delivery are stored in the storage section 14 by manual input, it is preferable that, as to the data representative of the physical condition before the delivery, i.e. in the non-pregnancy period or up to around 12th week in pregnancy, in order to cope with the daily variations of the physical condition, the data measured over about 1 week are stored in the storage section 14, averaged by the arithmetic processing section 10 and are stored in the storage section 14 to be used later.

Furthermore, although, in the present embodiment, the bioelectric characteristic in the non-pregnancy period or that in the 12th week of pregnancy is compared with the bio-electric characteristic on the measurement date after the delivery, the recovering condition may be represented more clearly when each of the measured data of the bioelectric characteristic after the delivery is associated with the date of the measurement into a set for each measurement day to be stored in the storage section 14 and the variation thereof is graphically represented.

Still further, although, in the present embodiment, the bioelectric characteristic of a woman in her puerperium is measured between her feet using an integral measuring apparatus with the body weight scale incorporated therein, the bioelectric characteristic may be measured between a hand and a foot or between hands since, between a hand and a foot or between hands, the same phenomenon in the bioelectric characteristic with that shown in FIG. 1 has been observed.

Yet further, although, in the present embodiment, the current from the current supply section 16 is constant current with single frequency of, for example, 50 KHz, the current with multi-frequencies may be applied for the measurement while sequentially switching the frequencies.

According to this invention, determination as to whether or not a puerperal woman has been recovered can be very easily made.

Since a bioelectric impedance or an interstitial fluid index may be used as a bioelectric characteristic of a woman on the basis of which a judgement is made as to whether or not the woman has been recovered according to this invention, a conventional body fat meter can be utilized for measuring such parameter.

What is claimed is:

1. A method for judging a recovery of physical condition of a puerperal woman comprising the steps of;
    measuring a bioelectric characteristic of the puerperal woman;
    storing a value of said bioelectric characteristic; and
    judging said recovery of physical condition of the puerperal woman based on a variation of said value.

2. A method for judging a recovery of physical condition of a pueperal woman in accordance with claim 1, wherein said bioelectric characteristic is a bioelectric impedance.

3. A method for judging a recovery of physical condition of a puerperal woman in accordance with claim 1, wherein said bioelectric characteristic is an interstitial fluid index.

4. A method for judging a recovery of physical condition of a puerperal woman after delivery comprising the steps of:
    measuring a bioelectric characteristic of the woman in non-pregnancy period or at an early stage of her pregnancy period;
    measuring the bioelectric characteristic of the puerperal woman; and
    comparing said bioelectric characteristics to judge the recovery of physical condition of the puerperal woman.

5. A method for judging a recovery of physical condition of a puerperal woman in accordance with claim 4, wherein said recovery of physical condition of the puerperal woman is judged by comparing said bioelectric characteristic of the woman in non-pregnancy period or at the early stage of her pregnancy period with a variation in the bioelectric characteristic value after her delivery.

6. A method for judging a recovery of physical condition of a puerperal woman in accordance with claim 5, wherein said bioelectric characteristic is a bioelectric impedance.

7. A method for judging a recovery of physical condition of a puerperal woman in accordance with claim 5, wherein said bioelectric characteristic is an interstitial fluid index.

8. A method for judging a recovery of physical condition of a puerperal woman comprising the steps of:
    measuring a bioelectric characteristic of the woman in non-pregnancy period or at an early stage of her pregnancy period;
    measuring the bioelectric characteristic of the puerperal woman;
    storing said bioelectric characteristics; and
    graphically indicating said bioelectric characteristics to facilitate a judgment of the recovery of physical condition of the puerperal woman.

9. A method for judging a recovery of physical condition of a puerperal woman in accordance with claim 8, wherein said bioelectric characteristics to be stored for her non-pregnancy period and for up to around 12th week in her pregnancy period is a mean value of the bioelectric characteristics averaged over around one week.

10. A method for judging a recovery of physical condition of a puerperal woman in accordance with claim 9, wherein said bioelectric characteristic is a bioelectric impedance.

11. A method for judging a recovery of physical condition of a puerperal woman in accordance with claim 9, wherein said bioelectric characteristic is an interstitial fluid index.

12. An apparatus for judging a recovery of a physical condition of a puerperal woman comprising:
    a measuring unit for measuring a bioelectric characteristic of the woman in a non-pregnancy period or at an early stage of her pregnancy period, and for measuring the bioelectric characteristic of the puerperal woman;
    a storing unit which stores measured values of said bioelectric characteristic measured by the measuring unit;
    a comparing unit which compares the measured value of said bioelectric characteristic of the woman in the non-pregnancy period or at the early stage of her pregnancy period with the measured value of said bioelectric characteristic of the puerperal woman; and
    an indicating unit for indicating the results of the comparison performed by said comparing unit.

13. An apparatus for judging a recovery of a physical condition of a puerperal woman in accordance with claim 12, wherein said storing unit is for storing said bioelectric characteristic of the woman in the non-pregnancy period or at the early stage of her pregnancy period and a daily bioelectric characteristic of the puerperal woman.

14. An apparatus for judging a recovery of a physical condition of a puerperal woman in accordance with claim 12 or 13, wherein said comparing unit is for calculating a ratio of the measured value of said bioelectric characteristic of the puerperal woman to the measured value of said bioelectric characteristic of the woman in the non-pregnancy period or at the early stage of her pregnancy period, and the indicating unit is for indicating said ratio.

15. An apparatus for judging a recovery of a physical condition of a puerperal woman in accordance with claim 12, 13, or 14, wherein said indicating unit is for indicating the measured values of said bioelectric characteristic.

16. An apparatus for judging a recovery of a physical condition of a puerperal woman in accordance with claims 12, 13, or 14, wherein said indicating unit is for graphically indicating the measured date dependency of said bioelectric characteristic.

17. An apparatus for judging a recovery of a physical condition of a puerperal woman in accordance with claims 12, 13, 14, 15 or 16, wherein the measured value of said bioelectric characteristic to be stored by said storing unit for the non-pregnancy period and for up to about the 12th week in her pregnancy period is a mean value of the bioelectric characteristic averaged over about one week.

18. An apparatus for judging a recovery of a physical condition of a puerperal woman in accordance with claims 12, 13, 14, 15, 16, or 17, wherein said bioelectric characteristic is the inverse number of an electric impedance.

19. An apparatus for judging a recovery of a physical condition of a puerperal woman in accordance with claims 12, 13, 14, 15, 16, or 17, wherein said bioelectric characteristic is an interstitial fluid index.

20. An apparatus for judging a recovery of a physical condition of a puerperal woman comprising:
    a measuring unit which measures a bioelectric characteristic of the puerperal woman;
    a storing unit which stores a value of said bioelectric characteristic and a date of measurement; and
    an indicating unit which indicates a variation of said values of said bioelectric characteristic in said storing unit.

21. An apparatus for judging a recovery of a physical condition of a puerperal woman in accordance with claim 20 further comprising a judging unit to judge a recovery of the physical condition of the puerperal woman based on said variation of said values of said bioelectric characteristic in said storing unit.

22. An apparatus for judging a recovery of a physical condition of a puerperal woman comprising:

a measuring unit for measuring a bioelectric characteristic of the woman in a non-pregnancy period or at an early stage of her pregnancy period and for measuring the bioelectric characteristic of the puerperal woman;

a storing unit which stores measured values of said bioelectric characteristic measured by the measuring unit;

a calculating unit which calculates a recovery rate based on the measured value of said bioelectric characteristic of the woman in the non-pregnancy period or at the early stage of her pregnancy period and the measured value of said bioelectric characteristic of the puerperal woman; and an indicating unit for indicating said recovery rate.

23. An apparatus for judging a recovery of a physical condition of a puerperal woman in accordance with claims 20, 21, or 22, wherein said bioelectric characteristic is bioelectric impedance.

24. An apparatus for judging a recovery of a physical condition of a puerperal woman in accordance with the claims 20, 21, or 22, wherein said bioelectric characteristic is an interstitial fluid index.

25. An apparatus for judging a recovery of a physical condition of a puerperal woman comprising:

a measuring unit which measures a bioelectric impedance of the puerperal woman; and a judging unit which judges the recovery of the physical condition of the puerperal woman based on the extent that said bioelectric impedance, which was lowered due to pregnancy, rose after delivery.

26. An apparatus for judging a recovery of a physical condition of a puerperal woman comprising:

an inputting unit which inputs a body weight;

a measuring unit which measures a bioelectric impedance;

a change-over switch for switching a function of said apparatus;

a calculating unit which calculates how said bioelectric impedance is recovering toward a bioelectric impedance measured in a non-pregnancy period or at an early stage of pregnancy when said change-over switch is switched to a weight scale mode for a pregnant woman, or calculates a body fat rate based on said body weight and said bioelectric impedance when said change-over switch is not switched to said weight scale mode for a pregnant woman.

27. An apparatus for judging a recovery of a physical condition of a puerperal woman in accordance with claim 26, wherein said change-over switch is a push button, and said change-over switch is switched to said weight scale mode for a pregnant woman when said change-over switch is pushed.

28. An apparatus for judging a recovery of a physical condition of a puerperal woman in accordance with claims 26 or 27, wherein said inputting unit is a body weight meter.

* * * * *